United States Patent
Nieuwoudt et al.

(10) Patent No.: US 11,396,487 B2
(45) Date of Patent: Jul. 26, 2022

(54) PROCESS OF MAKING PSEUDOIONONE AND HYDROXY PSEUDOIONONE IN AQUEOUS MIXTURES COMPRISING CITRAL AND ACETONE, COMPRISING ADDING FIRST AND SECOND AMOUNTS OF HYDROXIDE

(71) Applicant: BASF SE, Ludwigshafen am Rhein (DE)

(72) Inventors: Josias Jakobus Nieuwoudt, Ludwigshafen am Rhein (DE); Bernhard Brunner, Ludwigshafen am Rhein (DE); Sven Reining, Ludwigshafen am Rhein (DE); Timon Stork, Kuantan (MY); Bjoern Kaibel, Ludwigshafen am Rhein (DE); Alexander Zipp, Ludwigshafen am Rhein (DE); Oliver Bey, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/293,498

(22) PCT Filed: Nov. 13, 2019

(86) PCT No.: PCT/EP2019/081100
§ 371 (c)(1),
(2) Date: May 13, 2021

(87) PCT Pub. No.: WO2020/099452
PCT Pub. Date: May 22, 2020

(65) Prior Publication Data
US 2022/0048844 A1    Feb. 17, 2022

(30) Foreign Application Priority Data

Nov. 13, 2018  (EP) .................................... 18205994

(51) Int. Cl.
*C07C 45/74* (2006.01)

(52) U.S. Cl.
CPC .................................. *C07C 45/74* (2013.01)

(58) Field of Classification Search
CPC ..................................................... C07C 45/74
See application file for complete search history.

(56) References Cited

U.S. PATENT DOCUMENTS

| 3,840,601 A | 10/1974 | Gradeff |
| 4,431,844 A | 2/1984 | Janitschke et al. |
| 4,874,900 A * | 10/1989 | Mitchell .................. C07C 45/74 568/390 |

OTHER PUBLICATIONS

International Preliminary Report on Patentability received for PCT Patent Application No. PCT/EP2019/081100, dated May 27, 2021, 7 pages.
International Search Report and Written Opinion received for PCT Patent Application No. PCT/EP2019/081100, dated Feb. 18, 2020, 8 pages.

* cited by examiner

*Primary Examiner* — Sikarl A Witherspoon
(74) *Attorney, Agent, or Firm* — Faeger Drinker Biddle & Reath LLP (57) ABSTRACT

Described is a process of making pseudoionone and hydroxy pseudoionone comprising the steps of (i) preparing a first aqueous mixture comprising first concentrations of acetone, citral and hydroxide, (ii) producing a second aqueous mixture by allowing to react for a reaction time the components of the first aqueous mixture and (iii) producing a third aqueous mixture by adding to the second aqueous mixture a second amount of hydroxide so that an additional amount of pseudoionone is formed in the third aqueous mixture. The invention further suggests an apparatus for making pseudoionone and hydroxy pseudoionone as well as to a respective process and use of said apparatus in making pseudoionone and hydroxy pseudoionone.

20 Claims, 2 Drawing Sheets

PROCESS OF MAKING PSEUDOIONONE AND HYDROXY PSEUDOIONONE IN AQUEOUS MIXTURES COMPRISING CITRAL AND ACETONE, COMPRISING ADDING FIRST AND SECOND AMOUNTS OF HYDROXIDE

CROSS-REFERENCE TO RELATED APPLICATIONS

This application is a national stage application (under 35 U.S.C. § 371) of PCT/EP2019/081100, filed Nov. 13, 2019, which claims benefit of European Application No. 18205994.9, filed Nov. 13, 2018, both of which are incorporated herein by reference in their entirety.

The present invention relates to a process of making pseudoionone and hydroxy pseudoionone comprising the steps of (i) preparing a first aqueous mixture comprising first concentrations of acetone, citral and hydroxide; (ii) producing a second aqueous mixture by allowing to react for a reaction time the components of the first aqueous mixture and (iii) producing a third aqueous mixture by adding to the second aqueous mixture a second amount of hydroxide so that an additional amount of pseudoionone is formed in the third aqueous mixture. The present invention further relates to an apparatus for making pseudoionone and hydroxy pseudoionone as well as to a respective process and use of said apparatus in making pseudoionone and hydroxy pseudoionone.

Pseudoionone is a key intermediate in industrial syntheses of vitamins A and E and of carotinoids, e.g. for use in natural and nature-identical products, e.g. fragrances, flavors, nutritional products or dietary supplements.

Document NL 6704541 describes a process for preparing liquid, soluble condensation products by reacting ketones with aldehydes in the presence of alkaline condensing agents.

Document EP 0062291 A1 (an equivalent of U.S. Pat. No. 4,431,844 A) discloses an improved process for producing poly-unsaturated ketones.

Document WO 2004/041764 A1 describes a continuous process for producing pseudoionones and ionones.

Document WO 2005/056508 A1 pertains to a method for the production of tetrahydrogeranylacetone.

Document U.S. Pat. No. 3,840,601 deals with a process for preparation of methyl ionones.

In the light of the existing prior art there is still a need for a process of making pseudoionone and hydroxy pseudoionone, in particular pseudoionone, with increased efficiency, in particular with increased yield of pseudoionone, when compared with known processes. Moreover, there is still a need for an improved apparatus which can facilitate such process with increased efficiency.

Correspondingly, it was a primary object of the present invention to provide a process of making pseudoionone and hydroxy pseudoionone, in particular pseudoionone, which can be carried out as an industrial process, in particular as a continuous process and which provides increased efficiency, in particular an increased yield of pseudoionone.

It was another object of the present invention to provide an apparatus for making pseudoionone and hydroxy pseudoionone, in particular in continuous operation and which provides increased efficiency, in particular an increased yield of pseudoionone.

It has now been found that, under a first perspective, the primary object and other objects of the present invention can be accomplished by a process of making pseudoionone and hydroxy pseudoionone, preferably pseudoionone, comprising the following steps:

(P1) preparing a first aqueous mixture (i.e. a mixture comprising water) comprising first concentrations of acetone, citral and hydroxide, by combining first amounts of water, acetone, citral and hydroxide,

(P2) producing a second aqueous mixture (i.e. a mixture comprising water) by allowing to react for a reaction time the components of the first aqueous mixture so that pseudoionone, hydroxy pseudoionone and 4-hydroxy-4-methylpentan-2-one are formed, and
acetone, citral and hydroxide are consumed,
the second aqueous mixture comprising
4-hydroxy-4-methylpentan-2-one at a concentration which is higher than its concentration in the first aqueous mixture,
acetone, citral and hydroxide at second concentrations which are lower than their first concentrations, and
pseudoionone and hydroxy pseudoionone,
and (P3) producing a third aqueous mixture (i.e. a mixture comprising water) by adding to the second aqueous mixture a second amount of hydroxide so that an additional amount of pseudoionone is formed in the third aqueous mixture.

The invention as well as preferred variants and preferred combinations of parameters, properties and elements thereof are defined in the appended claims. Preferred aspects, details, modifications and advantages of the present invention are also defined and explained in the following description and in the examples stated below.

It has now been found that the process of making pseudoionone and hydroxy pseudoionone according to the present invention is highly efficient and is excellently suited for batch-wise, semi-batch-wise and, in particular, continuous performance. Surprisingly, it has been found that the process of the present invention results in an increased yield of pseudoionone when compared with similar processes known in the art. It has also been found that the process of the present invention shows an increased selectivity in the production or making of pseudoionone over hydroxy pseudoionone. Said increased selectivity is desirable as pseudoionone is a still more versatile intermediate product for industrial syntheses than hydroxy pseudoionone.

In the context of the present invention "pseudoionone", in accordance with the usual meaning in the technical field, means a mixture of the four isomers (3Z,5Z)-6,10-dimethyl-3,5,9-undecatrien-2-one, (3E,5Z)-6,10-dimethyl-3,5,9-undecatrien-2-one, (3Z,5E)-6,10-dimethyl-3,5,9-undecatrien-2-one and (3E,5E)-6,10-dimethyl-3,5,9-undecatrien-2-one. In the process according to the present invention, a mixture of all four of said isomers is usually formed. A mixture of all four of said isomers is often also referred to (including in this text) as 6,10-dimethyl-3,5,9-undecatrien-2-one with CAS® RN 141-10-6. One of the isomers of pseudoionone (i.e. (3E,5E)-6,10-dimethyl-3,5,9-undecatrien-2-one) is shown in formula I below as an example:

In the context of the present invention "hydroxy pseudoionone" means the compounds 4-hydroxy-6,10-dimethyl-undeca-5,9-dien-2-one and 4-hydroxy-6,10-dimethyl-undeca-6,9-dien-2-on, including their isomers. In the process according to the present invention, a mixture of four compounds, i.e. the two isomers (5E)-4-hydroxy-6,10-dimethyl-undeca-5,9-dien-2-one and (5Z)-4-hydroxy-6,10-dimethyl-undeca-5,9-dien-2-one and the two isomers (6E)-4-hydroxy-6,10-dimethyl-undeca-6,9-dien-2-one and (6Z)-4-hydroxy-6,10-dimethyl-undeca-6,9-dien-2-one is usually formed. At least some of said four compounds (probably (5E)-4-hydroxy-6,10-dimethyl-undeca-5,9-dien-2-one and/or (5Z)-4-hydroxy-6,10-dimethyl-undeca-5,9-dien-2-one) may subsequently at least partially degrade again under the conditions of the process according to the present invention. One of said four compounds (i.e. (5E)-4-hydroxy-6,10-dimethyl-undeca-5,9-dien-2-one) is shown in formula II below as an example:

(II)

In the context of the present invention "citral", also known as 3,7-dimethylocta-2,6-dienal (CAS® RN 5392-40-5), in accordance with the usual meaning in the technical field, means a mixture of the cis-trans isomers geranial, also known as (E)-3,7-dimethylocta-2,6-dienal (CAS® RN 141-27-5), and neral, also known as (Z)-3,7-dimethylocta-2,6-dienal (CAS® RN 106-26-3). Although the two separate isomers, geranial and neral, can also be used as starting compounds in the first aqueous mixture, like citral, their use is not preferred, mainly for commercial reasons. In addition, it has been found in own experiments that the reaction of the separate isomers neral or geranial, respectively, to pseudoionone (or pseudoionone isomers) proceeds faster than the isomerisation of the separate isomers to citral. By using a separate isomer (i.e. neral or geranial) in the process of the present invention it is therefore possible to produce pseudoionone enriched in certain isomers, however, it is not possible in this variant to produce single isomers of pseudoionone.

In the context of the present invention, the term "hydroxide" has its usual meaning in the technical field and denotes a hydroxide anion "HO⁻". Where the present text refers to the single term "hydroxide", this means the hydroxide anion, independent from any source for providing said hydroxide anion, e.g. a metal hydroxide like NaOH, or the exact nature of such metal hydroxide.

In the context of the present invention, the term "concentration" as used in the definitions of the first, second and/or third aqueous mixtures (in particular the concentrations of the components acetone, citral, hydroxide and/or 4-hydroxy-4-methylpentan-2-one) preferably refers to the total mass of a certain component (in particular the molar mass of the components acetone, citral, hydroxide and/or 4-hydroxy-4-methylpentan-2-one) relative to the total mass of water and acetone present in the aqueous mixture considered, unless expressly stated otherwise in this text.

In step (P1) of the process of the invention as defined above, preparing the first aqueous mixture as defined above corresponds to the start conditions of the process according to the present invention (i.e. at time "t=0" conditions).

The citral used for preparing the first aqueous mixture in step (P1) as defined above may be pure citral (e.g. with a purity of 97%) or it may be citral recycled from other processes or from the process of the invention. It has been found in own experiments that citral can—without a significant adverse effect on process performance—be used in step (P1) which has a purity of ≥92 wt.-%, preferably of ≥95 wt.-%, relative to the total weight of citral and organic impurities accompanying citral. Organic impurities accompanying citral are organic compounds other than citral which can only be separated from citral by additional purification steps. Such additional purification steps are, however, not preferred as they would usually also lead to a loss of citral.

In step (P1) of the process of the invention as defined above, 4-hydroxy-4-methylpentan-2-one may be present in the first aqueous mixture, e.g. in cases where reaction mixtures from other processes or from the process of the invention are used to prepare the first aqueous mixture, or 4-hydroxy-4-methylpentan-2-one may not be present in the first aqueous mixture.

In step (P2) of the process of the invention as defined above, acetone, citral and hydroxide are allowed to react so that pseudoionone, hydroxy pseudoionone and 4-hydroxy-4-methylpentan-2-one are formed and acetone, citral, and hydroxide are consumed. The reaction taking place in step (P2) is of an aldol condensation-type known in the art. 4-hydroxy-4-methylpentan-2-one (also known as diacetone alcohol, CAS® RN 123-42-2) is formed in step (P2) as a reaction product in a competitive reaction through self-condensation of acetone. As another side reaction, mesityloxide (also known as methylpent-3-en-2-one, CAS® RN 141-79-7) may be formed in step (P2) by elimination of water from 4-hydroxy-4-methylpentan-2-one. Further side products may subsequently be formed as is known in the art.

By formation of 4-hydroxy-4-methylpentan-2-one in step (P2), its concentration is in any case higher in the second aqueous mixture (step (P2)) than it is (or was) in the first aqueous mixture (step (P1)), irrespective of the concentration of 4-hydroxy-4-methylpentan-2-one that previously existed in the first aqueous mixture (and also in the case when no 4-hydroxy-4-methylpentan-2-one is or was present in the first aqueous mixture, see above).

In step (P2) of the process of the invention as defined above, acetone and citral are consumed mainly due to their reaction to form the reaction products, pseudoionone and hydroxy pseudoionone. Although hydroxide in the process according to the invention generally functions as a catalyst, in practice it can be observed that it is also consumed in the course of step (P2), for instance due to involvement in side reactions or competitive reactions as a Cannizzaro reaction. In order to compensate for hydroxide which is consumed in step (P2) and preferably to even increase the concentration of hydroxide, preferably the concentration of dissolved hydroxide, in the third aqueous mixture (when compared to the concentration of hydroxide or dissolved hydroxide in the first aqueous mixture), the second amount of hydroxide is added to the second aqueous mixture according to the process of the present invention.

Preferred is therefore a process according to the present invention as defined herein (or a process according to the invention as described above or below as being preferred), wherein in step (P3):
the second amount of hydroxide which is added to the second aqueous mixture is in the range of from 5 mass-% to 50 mass-%, preferably in the range of from 10 mass-% to 40 mass-%, of the first amount of hydroxide in the first aqueous mixture, and/or the concentration of dissolved hydroxide present in the third aqueous mixture is higher than the concentration of dissolved hydroxide present in the second aqueous mixture at the end of the reaction time.

If, for example, the first amount of hydroxide in the first aqueous mixture is 0.1 g, then the second amount of hydroxide which is added to the second aqueous mixture preferably is in the range of from 0.005 g to 0.05 g, more preferably in the range of from 0.01 g to 0.04 g.

It appears from own experiments that a second amount of hydroxide which is added to the second aqueous mixture in the magnitude as defined above under the conditions of the process according to the present invention results in a higher concentration of hydroxide which is or can be dissolved in the liquid phase of the third aqueous mixture than in the liquid phase of the first aqueous mixture. In own experiments, it has been found that the addition of said second amount of hydroxide to the second aqueous mixture leads to the most favourable results in terms of increased yield of pseudoionone and selectivity for the formation thereof with the process according to the invention.

Without wishing to be bound by any theory, it is presently assumed that the 4-hydroxy-4-methylpentan-2-one which is formed in step (P2) contributes to an increased solubility of the hydroxide in the second aqueous mixture and/or in the third aqueous mixture (relative to the solubility of the hydroxide in the first aqueous mixture) and that this increased solubility of hydroxide contributes to the beneficial results of the process of the present invention in terms of yield and selectivity for the main product (the main product being pseudoionone). It was further found that the highest solubility of hydroxide (and thus the highest beneficial effect as explained above) is accomplished when the concentration of 4-hydroxy-4-methylpentan-2-one in the second aqueous mixture has reached its maximum value or has reached a value close to its maximum value (in particular a value of ≥80%, preferably of ≥85% of its maximum), and before the concentration of 4-hydroxy-4-methylpentan-2-one in the second aqueous mixture declines again in the course of the reaction, e.g by reverse reaction (as is usually occurring in chemical equilibrium reactions).

It is therefore preferred to add the second amount of hydroxide to the second aqueous mixture when the concentration of 4-hydroxy-4-methylpentan-2-one in the second aqueous mixture has reached a value of ≥80%, preferably of ≥85% of its maximum value and/or before the concentration of 4-hydroxy-4-methylpentan-2-one in the second aqueous mixture has declined (again) to a value of ≤80%, preferably of ≤85%, of its maximum value. Correspondingly, the second amount of hydroxide is added to the second aqueous mixture in step (P3) when the concentration of 4-hydroxy-4-methylpentan-2-one in the second aqueous mixture has a value of ≥80%, preferably of ≥85% of its maximum value.

A process according to the present invention is therefore preferred as defined herein (or a process according to the invention as described above or below as being preferred), wherein the second amount of hydroxide is added to the second aqueous mixture in step (P3):

when the molar concentration of 4-hydroxy-4-methylpentan-2-one in the second aqueous mixture has reached a value of 70 mmol/l or above;
and/or
before the concentration of 4-hydroxy-4-methylpentan-2-one in the second aqueous mixture has reached a maximum or when the concentration of 4-hydroxy-4-methylpentan-2-one in the second aqueous mixture has reached a maximum;
and/or
when the concentration of 4-hydroxy-4-methylpentan-2-one in the second aqueous mixture has a value of ≥80%, preferably of ≥85% of its maximum value;
and/or
3 minutes or more, preferably 5 minutes or more, after the first aqueous mixture has been prepared (i.e. when all components, water, acetone, citral and hydroxide, have been combined in step (P1)), and preferably less than 25 minutes, more preferably less than 20 minutes and yet more preferably less than 15 minutes after the first aqueous mixture has been prepared;
and/or
after 3 minutes or more, preferably after 5 minutes or more, of reaction time of the components of the first aqueous mixture in step (P2), and preferably after less than 25 minutes, more preferably after less than 20 minutes and yet more preferably after less than 15 minutes, of reaction time of the components of the first aqueous mixture in step (P2);
and/or
when the molar ratio of 4-hydroxy-4-methylpentan-2-one:acetone in the second aqueous mixture has reached a value in the range of from 1:45 to 1:8.

In the preferred variant of the process according to the present invention wherein the second amount of hydroxide is added to the second aqueous mixture in step (P3) when the molar concentration of 4-hydroxy-4-methylpentan-2-one in the second aqueous mixture has reached a value of 70 mmol/l or above, the molar concentration of 4-hydroxy-4-methylpentan-2-one in the second aqueous mixture is the total molar amount of 4-hydroxy-4-methylpentan-2-one relative to the total volume of water and acetone present in the second aqueous mixture.

It has been found in own experiments that the time interval of 3 minutes or more, preferably of 5 minutes or more, of reaction time of the components of the first aqueous mixture in step (P2) before the second amount of hydroxide is added to the second aqueous mixture in step (P3) usually provides for a beneficial compromise between desired residence time (as short as possible for reasons of process efficiency) on one hand side and good conversion rate in step (P2) on the other hand side. It has also been found in own experiments that said time interval of 3 minutes or more, preferably of 5 minutes or more, of reaction time of the components of the first aqueous mixture in step (P2) before the second amount of hydroxide is added to the second aqueous mixture in step (P3) usually correlates with the time interval in which the concentration of 4-hydroxy-4-methylpentan-2-one in the second aqueous mixture has reached a value of ≥80%, preferably of ≥85% of its maximum value (as explained above).

In the context of the present invention, the concentration of 4-hydroxy-4-methylpentan-2-one in the second aqueous mixture and its variation is preferably determined by gas chromatography, more preferably by a calibrated gas chromatography method. For this purpose, a sample of the second aqueous mixture is drawn and neutralized (preferably with diluted aqueous acetic acid) and then the concentration of 4-hydroxy-4-methylpentan-2-one is determined in the neutralized sample as is known in the art. For determining the maximum value of the concentration of 4-hydroxy-4-methylpentan-2-one in the second aqueous mixture or generally the change of the concentration of 4-hydroxy-4-methyl-pentan-2-one in the second aqueous mixture over time, samples can be drawn in time intervals from the second aqueous mixture and analysed for their concentration of 4-hydroxy-4-methylpentan-2-one as a function of time. From the results received, reference values can be determined and standardized (e.g. as calibration curves) for predicting the progression of the concentration of 4-hydroxy-4-methylpentan-2-one in the second aqueous mixture under various process conditions.

In the context of the present invention the molar ratio of 4-hydroxy-4-methylpentan-2-one:acetone in the second aqueous mixture and its variation is preferably determined by gas chromatography as explained here above. Alternatively, the molar ratio of 4-hydroxy-4-methylpentan-2-one: acetone in the second aqueous mixture and its variation is determined by $^1$H-NMR spectroscopy and integration of the relevant signals for the target compounds, as is generally known in the art. Both methods will find essentially the same results with the deviations not being significant for practical purposes.

For enhanced performance of the process according to the present invention it is expedient to provide for intimate mixing of the hydroxide into the first and/or second aqueous mixtures (preferably at its respective dosing point or at the location where dosing of the hydroxide into the first and/or second aqueous mixture takes place), e.g. to facilitate best possible dissolution and distribution of the hydroxide in said aqueous mixtures.

A process according to the present invention is therefore preferred as defined herein (or a process according to the invention as described above or below as being preferred), wherein the first aqueous mixture and/or the second aqueous mixture and/or the third aqueous mixture are mixed or agitated mechanically. Where the process according to the invention is conducted continuously at least for a part of the process or process time, the mixing can e.g. be done by integrating a static mixer in the reactor at the desired positions. Where the process according to the invention is conducted batch-wise or semi-batch-wise at least for a part of the process or process time, the mixing can e.g. be done by a mechanical stirrer.

In the context of the present invention, a "part of the process" according to the invention preferably means any of steps (P1), (P2) and (P3) individually or a combination of two of said steps.

It has been found in own experiments that the process according to the invention is particularly suitable for continuous performance which is most convenient for an industrial process in terms of production efficiency.

A process according to the present invention is therefore preferred as defined herein (or a process according to the invention as described above or below as being preferred), wherein
at least a part of the process, preferably the entire process, is conducted continuously (in flow mode), preferably in a tube reactor, more preferably in a tube reactor showing a flow regime which is as close as possible to plug-flow behaviour;
and/or
the second amount of hydroxide is added to the second aqueous mixture continuously.

Where at least a part of the process, preferably the entire process, is conducted continuously in a tube reactor, said tube reactor preferably shows a behavior which at least approximates plug flow behavior.

In some cases, a process according to the present invention is also preferred as defined herein (or a process according to the invention as described above or below as being preferred), wherein at least a part of the process, preferably the entire process, is conducted discontinuously, preferably in batch-mode or semi-batch mode.

In certain cases, a process according to the present invention is also preferred as defined herein (or a process according to the invention as described above or below as being preferred), wherein the second amount of hydroxide is added to the second aqueous mixture in one single portion or in several individual portions, preferably in one single portion. This variant of the process according to the invention can be applied in continuous mode, batch mode and/or semi-batch mode operation of the process.

It has been found in own experiments that the average reaction rate for forming pseudoionone and the total amount of pseudoionone that is formed as a result of the reaction are both higher in the process according to the present invention than in similar processes of the prior art, i.e. for the same volume and residence time, more pseudoionone is formed in a process according to the present invention than in a similar process of the prior art which does not make use of the present invention.

A process according to the present invention is therefore preferred as defined herein (or a process according to the invention as described above or below as being preferred), wherein the total amount of pseudoionone formed in a sequence of steps (P2) and (P3) in a reaction time t [(P2)+(P3)] is higher than the total amount of pseudoionone formed in an isolated step (P2) in an equal reaction time t [(P2)+(P3)].

In the definition provided above, the term "t [(P2)+(P3)]" means the reaction time it takes for performing the steps (P2) and (P3) as defined above and below.

Preferred is furthermore a process according to the present invention as defined herein (or a process according to the invention as described above or below as being preferred), wherein the total process time is in the range of from ≥9 to ≤30 minutes, preferably in the range of from ≥12 to ≤25 minutes and more preferably in the range of from >12 to ≤20 minutes.

In the context of the present invention, the term "total process time" means the total time it takes for conducting a process according to the invention, i.e. a process comprising the steps (P1), (P2) and (P3). Where the process according to the present invention is conducted continuously, preferably over the entire process time, the total process time preferably corresponds to the residence time in a continuous reactor, preferably in a tube reactor. Where the process according to the present invention is conducted batch-wise or semi-batch-wise, preferably over the entire process time, the total process time preferably corresponds to the (total) reaction time in a batch (or semi-batch) reactor.

Preferred is also a process according to the present invention as defined herein (or a process according to the invention as described above or below as being preferred), wherein
the first concentration of the hydroxide in the first aqueous mixture is in the range of from 0.0015 to 0.02 mass-%, preferably of from 0.0015 to 0.0140 mass-%, more preferably in the range of from 0.0017 to 0.0070 mass-% and even more preferably in the range of from 0.0020 to 0.0065 mass-%, relative to the total mass of water and acetone present in the first aqueous mixture; and/or the molar ratio of the first amount of hydroxide present in the first aqueous mixture relative to the first amount of citral present in the first aqueous mixture is in the range of from 1.0 to 30.0 mmole/mole, preferably in the range of from 2.0 to 20.0 mmole/mole and more preferably in the range of from 2.0 to 12.0 mmole/mole;

and/or the molar ratio of the total amount of acetone present in the first aqueous mixture relative to the total amount of citral present in the first aqueous mixture is in the range of from 24.0:1 to 65.5:1, preferably in the range of from 31.5:1 to 65.5:1, more preferably in the range of from 35.0:1 to 60.0:1, and yet more preferably in the range of from 37.5:1 to 50.0:1.

In a particularly preferred variant of the process of the present invention as defined herein (or a process according to the invention as described above or below as being preferred), the molar ratio of the total amount of acetone present in the first aqueous mixture relative to the total amount of citral present in the first aqueous mixture is in the range of from 38.0:1 to 47.0:1.

It has been found in own experiments that the above-stated concentration or preferred concentration of the hydroxide in the first aqueous mixture is suited for allowing complete or substantially complete dissolution of the hydroxide in the first aqueous mixture and for allowing 4-hydroxy-4-methylpentan-2-one to be formed at a favourable rate and concentration in the second aqueous mixture. In a preferred variant of the process of the present invention, the first concentration of hydroxide in the first aqueous mixture is adjusted to be the maximum concentration of hydroxide which is soluble in the first aqueous mixture (i.e. the maximum possible concentration of hydroxide is used in step (P1) which can be completely dissolved in the first aqueous mixture).

It has also been found in own experiments that the above-stated ratios of the "first amount of hydroxide present in the first aqueous mixture":"first amount of citral present in the first aqueous mixture" and of the "total amount of acetone present in the first aqueous mixture":"total amount of citral present in the first aqueous mixture" in the above-stated ranges and preferred ranges contribute to an enhanced performance of the process according to the present invention. Ranges and preferred ranges of the above-stated concentration and ratios can preferably be combined. Where preferred ranges of the above-stated concentration and ratios are combined with each other, the combination also results in a preferred or even more preferred variant of the process of the present invention.

Preferred is also a process according to the present invention as defined herein (or a process according to the invention as described above or below as being preferred), wherein the first amount of hydroxide which is used to prepare the first aqueous mixture (step (P1)) and/or the second amount of hydroxide which is (are) added to the second aqueous mixture (step (P3)) is provided (in each case, as applicable) by one or more metal hydroxides,
  wherein preferably
    the one or more metal hydroxides are selected from the group consisting of:
      alkali metal hydroxides, preferably LiOH, NaOH and KOH; and
      alkaline earth metal hydroxides, preferably $Mg(OH)_2$, $Ca(OH)_2$, $Sr(OH)_2$ and $Ba(OH)_2$,
    and wherein more preferably the one or one of the more metal hydroxides is an alkali metal hydroxide, yet more preferably selected from the group consisting of LiOH, NaOH and KOH,
    and wherein most preferably the one or at least one of the more metal hydroxides is NaOH;
and/or (preferably "and")
the one or more metal hydroxides comprise one or more metal hydroxides dissolved in a liquid phase,
  wherein preferably the one or more metal hydroxides comprise one or more aqueous metal hydroxides,
  and wherein more preferably the one or more metal hydroxides are provided in the form of an aqueous solution of one or more metal hydroxides,
    wherein preferably the aqueous solution has a concentration of hydroxide ions in the range of from 0.3 to 1.5 mass-%, preferably in the range of from 0.35 to 0.65 mass-% and more preferably in the range of from 0.4 to 0.6 mass-%, relative to the total mass of water and metal hydroxides present in the aqueous solution.

In the variant of the process according to the invention as defined above, the one or more metal hydroxides dissolved in a liquid phase may be dissolved in any solvent or mixture of solvents which is suitable to dissolve the one or more metal hydroxides in the quantities as required or preferred for the process according to the present invention and which is compatible or does not interfere with the performance of the process. Quantities of the one or more metal hydroxides as required or preferred for the process according to the present invention are preferably quantities which provide a concentration of hydroxide ions in the liquid phase in the range of from 0.3 to 1.5 mass-%, preferably in the range of from 0.35 to 0.65 mass-% and more preferably in the range of from 0.4 to 0.6 mass-%, relative to the total mass of solvent or mixture of solvents and metal hydroxides present in the liquid phase.

In a preferred variant of the process according to the present invention, the one or more metal hydroxides comprise one or more metal hydroxides dissolved in a liquid phase, wherein the liquid phase comprises one or more solvents selected from the group consisting of water, acetone, alcohols comprising one to three carbon atoms and mixtures thereof. Preferred are solvents or mixtures of solvents which are already present in the process, in particular water, acetone and mixtures thereof.

In the preferred variant of the process according to the invention as defined above, an aqueous metal hydroxide preferably means a solution of one or more metal hydroxides comprising water. Said aqueous metal hydroxide can comprise (in addition to water) water-miscible solvents, preferably selected from the group consisting of methanol, ethanol and acetone. Preferred is an aqueous metal hydroxide which is a solution of one or more metal hydroxides in water or in a mixture of water and acetone.

In the variant of the process according to the invention as defined above, the one or more metal hydroxides may be provided by one or more metal hydroxides of varying degrees of purity. Preferred are one or more metal hydroxides with a purity of ≥70 mass-%, preferably of ≥85 mass-%, more preferably of ≥90 mass-% and even more preferably of ≥95 mass-%. Metal hydroxides which are of a lower grade of purity ("technical grades", e.g. with a purity ≤90 mass-%) may be used in the process of the present invention to the extent the impurities present in the metal hydroxides are compatible with or do not interfere with the performance of the process (e.g. because they are not properly dissolved in the liquid or aqueous phase as defined above and below).

Preferred is therefore also a process according to the present invention as defined herein (or a process according to the invention as described above or below as being preferred), wherein the first amount of hydroxide which is used to prepare the first aqueous mixture (step (P1)) and/or the second amount of hydroxide which is (are) added to the second aqueous mixture (step (P3)) is provided (in each case, as applicable) by one or more metal hydroxides,
wherein
the one or more metal hydroxides are selected from the group consisting of:
alkali metal hydroxides, preferably LiOH, NaOH and KOH;
wherein more preferably the one or one of the more metal hydroxides is an alkali metal hydroxide, yet more preferably selected from the group consisting of LiOH, NaOH and KOH,
wherein most preferably the one or at least one of the more metal hydroxides is NaOH;
and/or (preferably "and")
the one or more metal hydroxides are provided as an aqueous solution of one or more metal hydroxides,
wherein preferably the aqueous solution has a concentration of hydroxide ions in the range of from 0.3 to 1.5 mass-%, preferably in the range of from 0.35 to 0.65 mass-% and more preferably in the range of from 0.4 to 0.6 mass-%, relative to the total mass of water and metal hydroxides present in the aqueous solution.

Preferably, at least the second amount of hydroxide which is added to the second aqueous mixture (step (P3)) is provided by one or more metal hydroxides as defined here above.

In the preferred variants of the process according to the invention as defined here above, preferably the aqueous solution of one or more metal hydroxides is a solution in water or a solution in a mixture of water and acetone.

In the preferred variants of the process according to the present invention as defined here above, the preferred metal hydroxide(s) and the preferred forms of aqueous metal hydroxides, in particular the preferred form of an aqueous solution of metal hydroxides and the preferred concentration of hydroxide ions in said aqueous solution of one or more metal hydroxides, can be combined to result in particularly preferred variants of the process according to the present invention.

In one preferred variant of the process of the present invention, the second amount of hydroxide which is added to the second aqueous mixture (step (P3)) is provided by an aqueous NaOH solution, preferably a solution of NaOH in water, which preferably has a concentration of hydroxide ions in the range of from 0.3 to 1.5 mass-%, preferably in the range of from 0.35 to 0.65 mass-% and more preferably in the range of from 0.4 to 0.6 mass-%, relative to the total mass of water and NaOH present in said aqueous NaOH solution.

It has been found in own experiments that NaOH provides particularly beneficial properties in terms of solubility and reaction performance so that the process according to the invention delivers particularly favourable results in terms of product yield, in particular in yield of pseudoionone, if NaOH (in particular an aqueous NaOH solution with the concentration or a preferred concentration as defined above) is used to provide the second amount of hydroxide (step (P3)).

In order to further proper mixing or agitating of the second and/or the third aqueous mixture (as explained above) it is expedient, in particular where the process of the present invention is conducted continuously for at least a part of the process or process time, to add (dose) the second amount of hydroxide to the second aqueous mixture (step (P3)) in the form of an aqueous solution of one or more metal hydroxides (as defined above) and at the smallest possible vessel or pipe diameter into a static mixer and/or with a sparger and/or with a liquid distributor.

A process according to the present invention as defined herein is also preferred (or a process according to the invention as described above or below as being preferred), wherein the first aqueous mixture and/or (preferably "and") the second aqueous mixture and/or (preferably "and") the third aqueous mixture form liquid phases below their boiling points
and wherein preferably
the reaction temperature in the first aqueous mixture and/or in the second aqueous mixture and/or in the third aqueous mixture is in the range of from 60 to 110° C., preferably in the range of from 70 to 100° C. and more preferably in the range of from 70 to 90° C.;
and/or
at least a part of the process, preferably the entire process, is conducted at a pressure, preferably at an absolute pressure, in the range of from 150 to 1000 kPa, preferably in the range of from 150 to 700 kPa, more preferably in the range of from 200 to 650 kPa and yet more preferably in the range of from 250 to 600 kPa;
and/or
at least a part of the process, preferably the entire process, is conducted under adiabatic conditions.

In a preferred variant of the process according to the present invention, the reaction temperature in the first aqueous mixture and in the second aqueous mixture and in the third aqueous mixture is in each case in the range of from 60 to 110° C., preferably in the range of from 70 to 100° C. and more preferably in the range of from 70 to 90° C.

In certain variants of the present invention a process (or a process according to the invention as described above or below as being preferred) is preferred wherein the first aqueous mixture and/or (preferably "and") the second aqueous mixture and/or (preferably "and") the third aqueous mixture form liquid phases below their boiling points and wherein the reaction temperature in the first aqueous mixture and/or in the second aqueous mixture and/or in the third aqueous mixture is in the range of from 72 to 95° C., preferably in the range of from 72 to 92° C.

Preferred is also a process according to the present invention as defined herein (or a process according to the invention as described above or below as being preferred), wherein the reaction conditions, preferably the concentrations of acetone, citral and/or hydroxide, are selected or adjusted so that the first aqueous mixture forms a single liquid phase and/or the second aqueous mixture forms a single liquid phase and/or the third aqueous mixture forms a single liquid phase. In a preferred variant of the present invention, said reaction conditions are selected or adjusted so that the first aqueous mixture, the second aqueous mixture and the third aqueous mixture each form a single liquid phase.

Moreover, a process according to the present invention as defined herein (or a process according to the invention as described above or below as being preferred) is preferred, wherein the total amount of hydroxide present in the third aqueous mixture is dissolved in the liquid phase. It has been found in own experiments that a particularly good result of the process of the present invention in terms of yield of pseudoionone is achieved when the hydroxide present in the third aqueous mixture is present in the highest possible concentration which is still or which can be dissolved in the third aqueous mixture.

A process according to the present invention as defined herein (or a process according to the invention as described above or below as being preferred) is also preferred, wherein the first aqueous mixture comprises water in a concentration in the range of from 3 to 9 mass-%, preferably in the range of from 4 to 8 mass-% and more preferably in the range of from 5 to 7 mass-%, relative to the total mass of water and acetone present in the first aqueous mixture.

In a preferred variant of the process of making pseudoionone and hydroxy pseudoionone according to the present invention, the pseudoionone which is formed in step (P3) is isolated from the reaction mixture and the remaining residual mixture after isolation of the pseudoionone is recycled—in total or in part—to the process and used for preparing a first aqueous mixture. In a particularly preferred variant of the process according to the present invention, the remaining residual mixture is further purified to obtain selected fractions thereof which are recycled to the process as desired and used for preparing a first aqueous mixture.

It has now further been found that, under a second perspective, one or more objects of the present invention can be accomplished by an apparatus according to aspect A1 (see below). The invention in particular suggests an apparatus for producing pseudoionone and hydroxy pseudoionone, comprising a first substantially vertically oriented reactor chamber arranged such that components flow through the first reactor chamber in a first flow direction, a second substantially vertically oriented reactor chamber in fluid communication with the first reactor chamber, and the second reactor chamber being oriented such that components flow through the second reactor chamber in a second flow direction different from the first flow direction, wherein the first reactor chamber is configured to receive a first component feed containing a first aqueous mixture through an inlet, and to produce a second aqueous mixture by allowing to react for a reaction time the components of the first aqueous mixture, wherein the apparatus comprises a mixing device positioned downstream of the first component feed inlet to the first reactor chamber and said apparatus being configured to add a second component feed to the first component feed when the second aqueous mixture has formed, and the second reactor chamber is configured to receive the first and second component feeds unified in the mixing device from the first reactor chamber and to produce a third aqueous mixture from the first and second aqueous mixtures.

Preferably, the mixing device is positioned inside the first reactor chamber, or inside the second reactor chamber, or in between the first and second reactor chamber.

The preferred embodiments, variants or combinations of the process under the first perspective described above apply mutatis mutandis to the apparatus under the second perspective described herein. Likewise, the preferred embodiments, variants or combinations of the apparatus under the second perspective described herein apply mutatis mutandis to the process under the first perspective.

A vertical orientation is understood to encompass the respective reactor chamber or chambers being oriented within +/−15° of being perpendicular to a ground surface on top of which the apparatus is installed.

An aqueous solution is understood to encompass a mixture comprising water.

The invention is based upon the realization that an increased yield can be achieved by additionally adding a second component feed to the first component feed after a certain reaction time has passed in the first reactor chamber. This is particularly achieved by integrating the mixing device into the first reactor chamber towards the downstream end thereof. If the first reactor chamber is an upward flow chamber, the mixing device preferably is located at a top end of the first reactor chamber. If the first reactor chamber is a downward flow chamber, the mixing device is preferably located at a bottom end of the first reactor chamber.

The first component feed preferably comprises first concentrations of acetone, citral and hydroxide. Particularly preferred, first amounts of water, acetone, citral and hydroxide are combined in the first component feed. Further preferably, the reaction of the components of the first component feed in the first reactor chamber produces pseudoionone, hydroxy pseudoionone and 4-hydroxy-4-methylpentan-2-one, wherein acetone, citral, and hydroxide are being consumed. The second aqueous mixture preferably comprises 4-hydroxy-4-methylpentan-2-one at a concentration which is higher than its concentration in the first aqueous mixture, acetone, citral and hydroxide at second concentrations which are lower than their first concentrations, and pseudoionone and hydroxy pseudoionone. Further preferably, the second component feed comprises a second amount of hydroxide so that an additional amount of pseudoionone is formed in the third aqueous mixture.

In a preferred embodiment, the first flow direction is oriented upwards, and the second flow direction is oriented downwards, or vice versa.

In a further preferred embodiment, the mixing device is positioned on an outlet end of the first reactor chamber. The mixing device preferably has an inlet and an outlet, wherein the outlet is positioned such that the third aqueous mixture flows directly into the second reactor chamber.

In a further preferred embodiment, an inlet to the first reactor chamber for receiving the first component feed is a first inlet, and the first reactor chamber further comprises a second inlet for receiving the second component feed, wherein the second component feed is positioned upstream from the mixing device. Preferably, the second inlet is positioned laterally on the first reactor chamber and is configured to introduce the second component feed into the first component feed at a section of the first reactor chamber where the second aqueous mixture has already formed due to its residence time in the reactor chamber until it reaches the respective point. Preferably, the second inlet comprises a number of outlet orifices oriented towards the mixing device. In general, the term "a number of" is understood to mean one element or a plurality of elements. For example, the number of outlet orifices may be one or more outlet orifices, such as 1 to 50 outlet orifices.

Further preferably, the second inlet is positioned immediately upstream of the mixing device, or at a predetermined distance upstream of the mixing device. This is understood to mean that the second inlet is positioned such that its outlet (or at least one of its outlets in case there are more than one) is located upstream of the mixing device. The predetermined distance is preferably selected such that the entire second component feed is drawn into the mixing device without prior backwards flow inside the first reactor chamber. For practical purposes, it has been found that a distance within a range of 50 cm or less in the flow direction of the first component feed from an inlet of the mixing device, particularly preferred 25 cm or less, reliably leads to the entire second component feed directly being entrained by the first component feed and drawn into the mixing device without prior unwanted backwards flow.

In general, when using the terms upstream and downstream with respect to the invention, upstream is understood to mean opposite to the direction of flow, i.e. towards the source of a stream, while downstream is understood to mean in the direction of flow, i.e. towards the destination of a stream.

In a further preferred embodiment, the first reactor chamber comprises a tapered section upstream of and tapered towards the inlet of the mixing device, preferably immediately upstream of the second inlet, for accelerating the flow speed of the second aqueous mixture. The tapering cross-section being located upstream of and tapered towards the inlet of the mixing device have the advantageous effect of accelerating the flow velocity inside the reactor chamber and in particular within the mixing device. An increased flow velocity improves the mixing result of the mixing device and contributes to obtaining a homogeneous mixture of acetone and hydroxide, thus avoiding an undesired segregation of hydroxide from the mixture.

The first reactor chamber preferentially comprises a number of—i.e. one or a plurality of—further mixing elements, or number of packings, upstream of the mixing device, the mixing elements configured to harmonize a residence time of the first component feed between the inlet to the first reactor and the mixing device. Under harmonizing, it is to be understood that mostly all portions of the first component feed, preferably all portions, have a uniform residence time inside the first reactor chamber. The mixing elements preferably comprise so-called x-type mixing elements which are provided in segments located in sequence to one another in the flow direction of the first component feed, respectively. Adjacent mixing elements are preferably installed at an offset angle, preferably in the range of 60° to 120°, further preferably at 90°. The mixing elements upstream of the mixing device contribute to providing an even fluid distribution and even component distribution within the first component feed and also aid in minimizing unwanted free convection and back mixing, thus harmonizing the residence time spent by the first component feed in the first reactor chamber to at least approximate plug-flow behavior. While plug-flow is generally understood to mean that a medium is moving through a conduit with constant velocity across the entire cross section of the conduit, the present invention applies the term more broadly. Plug-flow behavior in the context of this invention does not need to be achieved in exact terms. Instead, as is pointed out throughout this document, it is considered sufficient if the residence time of all media passing through the reactor chambers is substantially harmonic, with small and local variations in flow speed across portions of the reactor chamber diameters may be disregarded.

According to another embodiment, the inlet for the first component feed is in fluid communication with a feed line, the feed line being configured to generate the first component feed from a plurality of starter materials. Preferably, the feed line comprises a first mixer and a second mixer, wherein the first mixer is configured to combine a first starter material feed and a second starter material feed, and the second mixer is positioned downstream of the first mixer and configured to combine the unified first and second starter feeds coming from the first mixer with a third starter material feed into the first component feed.

One of the starter material feeds, for example the first starter material feed, preferably comprises citral. A further one of the starter material feeds, for example the second starter material feed, preferably comprises acetone, and another one of the starter material feeds, for example the third starter material feed, preferably comprises hydroxide.

The feed line further preferably comprises at least one heating device, preferably at least one heat exchanger, configured to heat the first and second starter material feeds to a predetermined temperature that is higher than a temperature of the third starter material feed.

Particularly preferred, at least one heating device is configured to heat the first and second starter materials as a function of the first, second and third starter material feed rates and the temperature of the third starter material feed such that the first component feed reaches a predetermined set point temperature prior to entering the first reactor chamber.

The at least one heating device is preferentially positioned in between the first and second mixers.

According to a further preferred embodiment, the second reactor chamber comprises an opening that is configured to be reversibly opened and closed with a corresponding cover, the opening being dimensioned for introducing a packing into the second reactor chamber, the packing preferably comprising or consisting of loose packing material. Loose packing material provides the benefit of being easier to install and yet affording no to little sacrifice in overall performance with comparison to structural packing materials. The packing material inside the second reactor chamber contributes to preventing undesired laminar flow or unwanted free convection (which may be caused by density variations, in particular at low flow velocities) across the second reactor chamber, and contributes to an overall even distribution of material inside the second reactor chamber.

In a particularly preferred embodiment, at least one of the first and second reactor chambers is a reactor tube. Preferably, both reactor chambers are reactor tubes.

The second reactor chamber is preferably at least partially formed as a ring chamber.

The aforementioned two embodiments may advantageously be combined in that the first reactor chamber and second reactor chamber are part of one common reactor, said reactor having an inner tube and an outer tube, wherein the first reactor chamber is delimited by a volume of the inner tube, and the second reactor chamber is delimited by a volume of the outer tube minus the volume of the inner tube. Preferably, the first reactor chamber as the inner tube of a double tube reactor has a smaller overall cross-section than the second reactor chamber. This again contributes to an increased flow velocity of the first and second component feeds in the first reactor chamber leading to better mixing and a reduced segregation of hydroxide from the reaction mixture.

A further advantage of the aforementioned arrangement of a ring chamber around the first reactor chamber is that the portion of the first reactor chamber that is surrounded by the ring chamber is automatically insulated at least to a degree from environmental influences such as ambient temperature. Also, the design of the inventive apparatus can be very space-saving compared to a more conventional setup having two reactor chambers positioned in series to one another and side-by-side e.g. in an industrial manufacturing environment.

In further preferred embodiments, at least one of the reactor chambers, preferably both reactor chambers, are formed from a plurality of tubular segments that are mounted in series to one another. This provides a modular design which is advantageous for maintenance and deinstallation purposes, inter alia.

The second reactor chamber comprises at least one outlet for withdrawing the third aqueous mixture from the apparatus. Preferably, the second reactor chamber comprises a plurality of these outlets, further preferably 2, 3, 4, 5, 6, 7, 8 or more of these outlets. In preferred embodiments having a plurality of outlets, at least some and preferably all of these outlets are distributed along the circumference of the reactor chamber. Particularly preferred, the outlets are distributed evenly along the circumference of the reactor chamber. Further preferably, the outlets are located at the same position—such as length or height, depending on the orientation of the reactor chamber—of the reactor chamber with respect to the flow path of the third aqueous mixture.

In further preferred embodiments of the apparatus, the outlets are in fluid communication with a downstream manifold that is configured to unite the respective partial feeds flowing through the outlets to one common outlet feed. The manifold preferably comprises at least one of: a collecting tube, a collecting ring, one or more Y-pieces, or a combination of several or all of the aforementioned.

In a further alternative embodiment, the second reactor chamber comprises at least one, and preferably a plurality of, flow guiding baffles. The at least one flow guiding baffle is preferably oriented parallel to the longitudinal axis, i.e. flow axis, of the second reactor chamber. Further preferably, the at least one flow guiding baffle extends at least along a portion of the longitudinal extension (i.e. in the direction of the longitudinal axis) of the second reactor chamber. In preferred variants, the second reactor comprises 2, 3, 4, 5, 6, 7, 8 or more of these baffles.

The preferred embodiments, variants or combinations of the process under the first perspective and of the apparatus under the second perspective described hereinabove apply mutatis mutandis to the process under the third perspective described hereinafter. Likewise, the preferred embodiments, variants or combinations of the process under the third perspective described hereinafter apply mutatis mutandis to the process under the first perspective and to the apparatus under the second perspective described hereinabove.

According to the invention, the apparatus under the second perspective of the present invention (or its preferred embodiments) is (are) configured and comprise(s) the means to execute the processes under the first and/or third perspectives. Likewise, according to the invention, the processes under the first and/or third perspectives (or their preferred variants as disclosed herein) are in preferred embodiments conducted by using the apparatus under the second perspective or its preferred embodiments described hereinabove.

The invention has hereinabove been described under a second perspective with respect to an apparatus. Under a third perspective, the invention accomplishes the previously mentioned one or more objects also by suggesting a further process of making pseudoionone and hydroxy pseudoionone, preferably in an apparatus as described hereinabove, comprising the steps of:
feeding a first component feed containing a first aqueous mixture into a first reactor chamber, the first aqueous mixture preferably comprising first concentrations of acetone, citral and hydroxide, preferably by combining first amounts of water, acetone, citral and hydroxide,
producing a second aqueous mixture by allowing to react for a reaction time the components of the first aqueous mixture, preferably so that pseudoionone, hydroxy pseudoionone and 4-hydroxy-4-methylpentan-2-one are formed, and acetone, citral, and hydroxide are consumed, the second aqueous mixture preferably comprising 4-hydroxy-4-methylpentan-2-one at a concentration which is higher than its concentration in the first aqueous mixture, acetone, citral and hydroxide at second concentrations which are lower than their first concentrations, and pseudoionone and hydroxy pseudoionone, and
adding a second component feed to the first component feed, preferably a second amount of hydroxide, inside the first reactor chamber, in particular when the second aqueous mixture has formed,
supplying the first and second component feeds to a second reactor chamber, and producing a third aqueous mixture by allowing the second aqueous mixture and the second component feed to react for a reaction time in the second reactor chamber, so that an additional amount of pseudoionone is formed in the third aqueous mixture in the second reactor chamber.

While the process discussed under the first perspective of the present invention has focused more on the chemical side of the invention, said further process of making pseudoionone and hydroxy pseudoionone according to the invention under the third perspective focuses mainly on the technical side of the invention. The process under the third perspective assumes the same benefits and advantages as the apparatus under the second perspective. The preferred embodiments of the apparatus discussed hereinabove are thus also preferred embodiments of the processes discussed herein and vice versa.

Preferably, said process of making pseudoionone and hydroxy pseudoionone according to the invention under the third perspective comprises the step of controlling the feed rate of the second component feed relative to the feed rate of the first component feed such that
the second amount of hydroxide which is added to the second aqueous mixture is in the range of from 5 mass-% to 50 mass-%, preferably in the range of from 10 mass-% to 40 mass-%, of the first amount of hydroxide in the first aqueous mixture,
and/or
the concentration of dissolved hydroxide present in the third aqueous mixture is higher than in the second aqueous mixture.

Further preferably, the process under the third perspective comprises the step of accelerating the flow speed of the second aqueous mixture prior to adding the second component feed.

In a further preferred embodiment, the process under the third perspective comprises the steps of:
generating the first component feed by combining a first starter material feed, preferably comprising citral, and a second starter material feed, preferably comprising acetone and subsequently combining the unified first and second starter feeds with a third starter material feed, preferably comprising hydroxide, into the first component feed.

The process under the third perspective of the present invention preferably further comprises the step of heating the first and second starter material feeds to a predetermined temperature that is higher than a temperature of the third starter material feed, preferably by heating the first and second starter materials as a function of the first, second and third starter material feed rates and the temperature of the third starter material feed such that the first component feed reaches a predetermined set point temperature prior to entering the first reactor chamber. The control towards the predetermined set point temperature contributes to an improvement in reactor performance.

In further preferred embodiments, the process under the third perspective comprises controlling a feed rate of the first component feed such that the first component feed has a predetermined residence time in the first reactor chamber before reaching the second reactor chamber and/or before the addition of the second component feed, preferably in the range of 3 minutes or more, further preferably of 5 minutes or more. This time interval provides for a beneficial compromise between short desired residence time on one hand side and good conversion rate in the first component feed on the other hand side.

Still further, the process under the third perspective preferentially comprises the step of harmonizing the residence time of the first component feed in the first reactor chamber by providing a number of—i.e. one or a plurality of— mixing elements.

In order to enable an optimized yield relative to input resources, the process under the third perspective contemplates process monitoring and control, and preferably comprises the steps of:

b1) determining at least one of:
an amount of hydroxide unwantedly accumulating inside the first reactor chamber,
an amount of citral entering the first reactor chamber;
an amount of citral at the outlet or downstream of the first reactor chamber,
an amount of citral at the outlet or downstream of the second reactor chamber,
an amount of water at the outlet or downstream of the second reactor chamber,
an amount of at least one of pseudoionone or hydroxy pseudoionone at the outlet or downstream of the first reactor chamber;
an amount of at least one of pseudoionone or hydroxy pseudoionone at the outlet or downstream of the second reactor chamber;
the reactor feed temperature of at least one of the first or second component feeds,
the reactor residence time of at least one of the first or second component feeds; or
a feed rate of the first component feed;
and
b2) if the amount or amounts determined in b1) fall outside of respective predetermined threshold ranges, increasing or decreasing at least one of:
the feed rate of the second component feed relative to the first component feed, or
the feed rate of that starter material feed which comprises hydroxide, preferably the third starter material feed, relative to the first component feed,
such that the amounts determined in b1) return to inside of the threshold range.

The aforementioned amounts are preferably obtained by way of measurement of their respective absolute quantities within a sample volume, or by measuring their concentrations within the respective feeds and calculating their amounts via the flow rates of the respective feeds.

The process under the third perspective preferably further comprises the step of providing a packing in the second reactor chamber. The packing may be a structural packing, but in a particularly preferred variant consists of or at least comprises loose packing material. The latter allows for ease of installation and achieves the desired functions of the packing in this context, a minimization of streaking or an undesired laminar flow, in other words free convection, and an overall improved distribution of the contents of the third aqueous mixture across the second reactor chamber.

The process under the third perspective preferably further comprises the step of determining a pressure difference between the first and second reactor chamber, preferably at a respective location upstream and downstream of the mixing device. By determining the pressure difference between the first and second reactor chamber, in particular by determining the pressure difference between the inlet side and the outlet side of the mixing device which is positioned at the outlet of the first reactor chamber, an operator may monitor whether the mixing device is functional or dysfunctional, for example due to clogging. Monitoring the pressure difference can be conducted at minimal device cost and allows for a quick decision making and replacement or repair.

EXAMPLES

The following examples are meant to further explain and illustrate the invention without limiting its scope. Examples 1 to 3 were carried out in laboratory equipment and batch mode, also serving as model reactions for conducting the processes of the present invention under the first and second perspectives in continuous mode. Additional experiments (in continuous mode) have been conducted (not shown) using an apparatus according to one of the embodiments under the second perspective of the present invention and/or a process according to one of the preferred embodiments under the first and/or third perspective of the invention. Such additional experiments have confirmed the beneficial results received in examples 2 and 3 as discussed below.

Example 1: Preparation of Pseudoionone and Hydroxy Pseudoionone (Comparative Experiment not According to the Invention)

A 50 ml glass autoclave (max. pressure load 1.2 MPa) fitted with ports for dosing (an aqueous solution of sodium hydroxide) under pressure and for drawing samples (from the reaction chamber) under pressure, and equipped with magnetic stirrer, oil bath, temperature measuring for the oil bath and temperature measuring for the reaction chamber was used for the following experiments (subsequently referred to as "the autoclave").

34.18 g of acetone with a water content of 5.9% (wt./wt.) and 2.005 g of citral (mixture of isomers, with a purity of 97.0% as determined by gas chromatography) were placed under a nitrogen atmosphere in the autoclave at room temperature. The resulting mixture was heated to a temperature of 75° C. (reaction chamber; oil bath temperature: 80° C.) and stirred vigorously at internal pressure. Then, 0.426 g of a 1.22% (wt./wt.) aqueous solution of sodium hydroxide (equivalent to 140 ppm NaOH, "first amount of hydroxide") were added via a syringe through the port for dosing under pressure and the syringe was purged several times with the mixture from the reaction chamber (t=0, preparation of first aqueous mixture).

After the addition of the aqueous solution of sodium hydroxide, samples were drawn from the reaction chamber (through the port for drawing samples under pressure) at t=0.25 min (i.e. immediately after adding the aqueous solution of sodium hydroxide) and 5 min, 15 min, 30 min and 60 min thereafter and the samples were immediately neutralized with diluted aqueous acetic acid in each case. The neutralized samples were analysed by means of wt.-% calibrated gas chromatography for (i) conversion of citral, (ii) selectivity for formation of pseudoionone and (iii) selectivity for formation of hydroxy pseudoionone.

The results from these analyses are shown in table 1, below.

In this table (as well as in tables 2 and 3 below), "conversion citral [%]" means the proportion (percentage) of citral that had been converted after the respective time period, "selectivity pseudoionone [%]" means the percentage of the converted citral that had been converted to pseudoionone after the respective time period (where "pseudoionone" is as defined above) and "selectivity hydroxy pseudoionone [%]" means the percentage of the converted citral that had been converted to hydroxy pseudoionone after the respective time period (where "hydroxy pseudoionone" is as defined above).

TABLE 1

Conversion of citral and acetone to pseudoionone and hydroxy pseudoionone (comparative experiment)

| Time [min.] | Conversion citral [%] | Selectivity pseudoionone [%] | Selectivity hydroxy pseudoionone [%] |
| --- | --- | --- | --- |
| 0.25 | 22.9 | 19.5 | 4.6 |
| 5 | 77.2 | 79.6 | 4.4 |
| 10 | n.d. | n.d. | n.d. |
| 15 | 94.7 | 85.6 | 2.6 |
| 30 | 96.7 | 85.5 | 2.2 |
| 60 | 96.9 | 85.0 | 2.2 |

"n.d." means that no data point has been determined in this case.

Example 2: Preparation of Pseudoionone and Hydroxy Pseudoionone (Process According to the Invention)

An experiment according to example 1 (above) was performed, with the difference that an additional amount of hydroxide ("second amount of hydroxide") was added 5 min after the dosing of the first aqueous solution of sodium hydroxide ("first amount of hydroxide") had taken place. As the second amount of hydroxide, 105 mg of a 1.2% (wt./wt.) aqueous solution of sodium hydroxide (equivalent to 35 ppm NaOH) were added via a syringe in a manner analogous as described in example 1 above (cf. addition of the "first amount of hydroxide").

Samples were again drawn from the reaction chamber in a manner as described in example 1 above, at t=0.25 min (i.e. immediately after addition of the first dosing of aqueous solution of sodium hydroxide, i.e. after addition of the "first amount of hydroxide") and 5 min (i.e. immediately after addition of the second dosing of aqueous solution of sodium hydroxide, i.e. after addition of the "second amount of hydroxide"), 10 min, 15 min, 30 min and 60 min after the addition of said first dosing of aqueous solution of sodium hydroxide. The samples were again immediately neutralized and analysed by gas chromatography as described in example 1 above.

The results from these analyses are shown in table 2 below.

TABLE 2

Conversion of citral and acetone to pseudoionone and hydroxy pseudoionone (process according to the invention)

| Time [min.] | Conversion citral [%] | Selectivity pseudoionone [%] | Selectivity hydroxy pseudoionone [%] |
| --- | --- | --- | --- |
| 0.25 | 20.4 | 18.5 | 5.2 |
| 5 | 76.7 | 80.1 | 4.2 |
| 10 | 91.9 | 85.3 | 2.9 |
| 15 | 96.3 | 86.8 | 2.2 |
| 30 | 98.5 | 86.5 | 1.6 |
| 60 | 98.9 | 86.5 | 1.1 |

From the results in table 2 above it can be seen that the process according to the invention shows an increased reaction rate (see e.g. values of citral conversion after 15 min for the process according to the invention is 96.3%, compared with 94.7% for a comparative process according to table 1), an increased yield of the main product pseudoionone (see e.g. values for selectivity for formation of pseudoionone after 15 min for the process according to the invention is 86.8% (equivalent to 83.6% yield of pseudoionone), compared with 85.6% (equivalent to 81.1% yield of pseudoionone) for a comparative process according to table 1) and a beneficially decreased selectivity for the formation of hydroxy pseudoionone (see e.g. respective values after 15 min for the process according to the invention is 2.2%, compared with 2.6% for a comparative process according to table 1), when compared with a similar process not according to the invention (see example 1, above).

Example 3: Preparation of Pseudoionone and Hydroxy Pseudoionone (Process According to the Invention)

An experiment according to example 2 (above) was performed, with the only difference that the additional amount of hydroxide ("second amount of hydroxide") was added 10 min after the dosing of the first aqueous solution of sodium hydroxide ("first amount of hydroxide") had taken place. The sample at t=10 min was drawn immediately after addition of the second dosing of aqueous solution of sodium hydroxide, i.e. after addition of the "second amount of hydroxide".

The results from this example 3 are shown in table 3 below:

TABLE 3

Conversion of citral and acetone to pseudoionone and hydroxy pseudoionone (process according to the invention)

| Time [min.] | Conversion citral [%] | Selectivity pseudoionone [%] | Selectivity hydroxy pseudoionone [%] |
| --- | --- | --- | --- |
| 0.25 | 21.4 | 19.2 | 6.8 |
| 5 | 76.7 | 80.6 | 4.2 |
| 10 | 92.1 | 84.8 | 2.8 |
| 15 | 96.5 | 85.7 | 2.2 |
| 30 | 98.9 | 86.9 | 1.5 |
| 60 | 99.3 | 85.9 | 1.2 |

From the results in table 3 above it can be seen that the process according to the invention also shows an increased reaction rate (see e.g. values of citral conversion after 15 min for the process according to the invention is 96.5%, compared with 94.7% for a comparative process according to table 1), an increased yield of the main product pseudoionone (see e.g. values for selectivity for formation of pseudoionone after 15 min for the process according to the invention is 85.7% (equivalent to 82.7% yield of pseudoionone), compared with 85.6% (equivalent to 81.1% yield of pseudoionone) for a comparative process according to table 1) and a beneficially decreased selectivity for the formation of hydroxy pseudoionone (see e.g. respective values after 15 min for the process according to the invention is 2.2%, compared with 2.6% for a comparative process according to table 1), when compared with a similar process not according to the invention (see example 1, above).

DESCRIPTION OF A PREFERRED EMBODIMENT

A preferred embodiment of the invention, in particular of an apparatus under the second perspective of the present invention, will be described hereinafter in detail with reference to the accompanying drawings, wherein.

Figure 1:
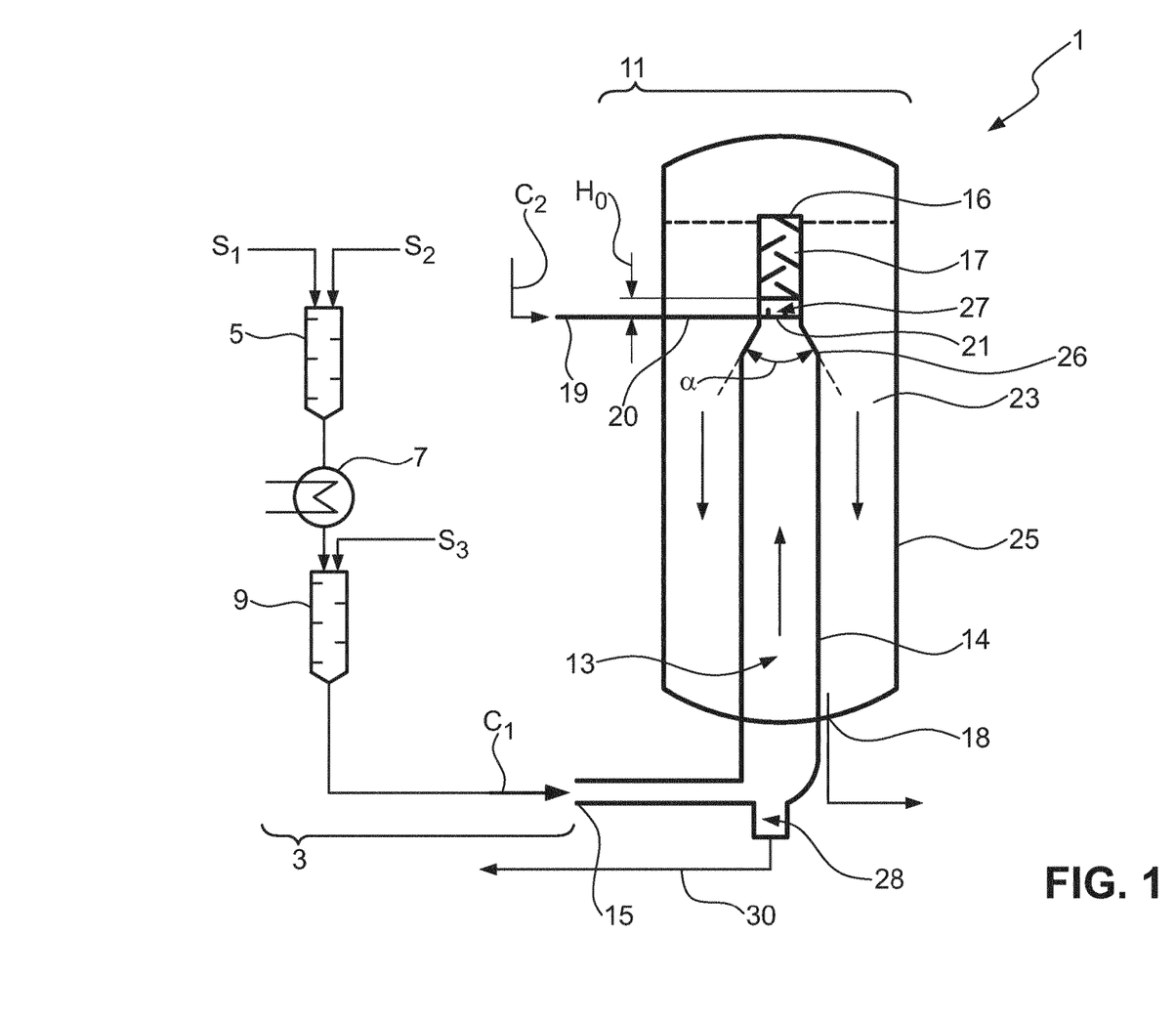
FIG. 1: is a schematic view of an apparatus for making pseudoionone and hydroxy pseudoionone according to a preferred embodiment.

FIG. 1 depicts an apparatus 1 for making pseudoionone and hydroxy pseudoionone according to the invention as described in general terms hereinabove. The apparatus 1 comprises a feed line 3 for generating a first component feed $C_1$. The feed line 3 comprises a first mixer 5 which is configured to receive and combine a first starter material feed $S_1$ and a second starter material feed $S_2$, wherein the first starter material feed $S_1$ preferably contains citral, and the second starter material feed $S_2$ preferably contains acetone.

Downstream of the first mixer 5, the feed line 3 comprises a heat exchanger 7 configured to heat the combined first and second starter material feed $S_1+S_2$ to a predetermined temperature. Downstream thereof, the feed line 3 comprises a second mixer 9 configured to combine the first and second starter material feed $S_1+S_2$ with a third starter material feed $S_3$, preferably comprising hydroxide. The temperature of the third starter material feed $S_3$ is preferably lower than the temperature of the first and second starter material feeds $S_1+S_2$ downstream of the heat exchanger 7. Therewith the first component feed $C_1$ exiting the second mixer 9 preferably may be controlled to have a predetermined set point temperature.

The apparatus 1 comprises a reactor 11 which in the preferred embodiment is a double tube reactor. The reactor 11 comprises a first reactor chamber 13 having an inlet 15 and an outlet 16. The outlet 16 is at the same time the outlet portion of a mixing device 17 located on the outlet end of the first reactor chamber 13. The first reactor chamber 13 is delimited by an inner tube 14 of the reactor 11.

The reactor 11 further comprises a second reactor chamber 23 which is delimited by an outer tube 25 and the inner tube 14 of the reactor 11 and has a substantially annular shape in the region where the inner tube 14 and outer tube 25 overlap. The outlet 16 of the first reactor chamber 13 is at the same time the inlet to the second reactor chamber 23. The second reactor chamber 23 further comprises an outlet 18 configured to withdraw material from the reactor 11. While in the embodiment shown here, the second reactor chamber comprises exactly one main outlet 18, it shall be understood that the second reactor chamber is designed to comprise at least one outlet 18, and in preferred embodiments may comprise a plurality of outlets 18, meaning two, three, four, five, six, seven, eight or more outlets 18.

The inlet 15 located at the bottom end of the first reactor chamber 13 is a first inlet, and the reactor 11 further comprises a second inlet 19 upstream from the mixing device 17, wherein the second inlet 19 is configured to receive a second component feed $C_2$ and to distribute the second component feed $C_2$ towards the mixing device 17. In order to accomplish this, the second inlet 19 comprises a feed tube 20 that is positioned within a distance $H_0$ of preferably 50 cm or less upstream of the inlet to the mixing device 17. The feed tube 20 comprises a number of—i.e. one or a plurality of—distribution outlets 21, each having an orifice 27 oriented towards the mixing device 17.

Upstream of the mixing device 17, the first reactor chamber 13 comprises a tapered section 26 which is tapered an angle α towards the mixing device 17, effective to increase the flow velocity of the first component feed C1 flowing through the first reactor chamber 13.

Figure 2:
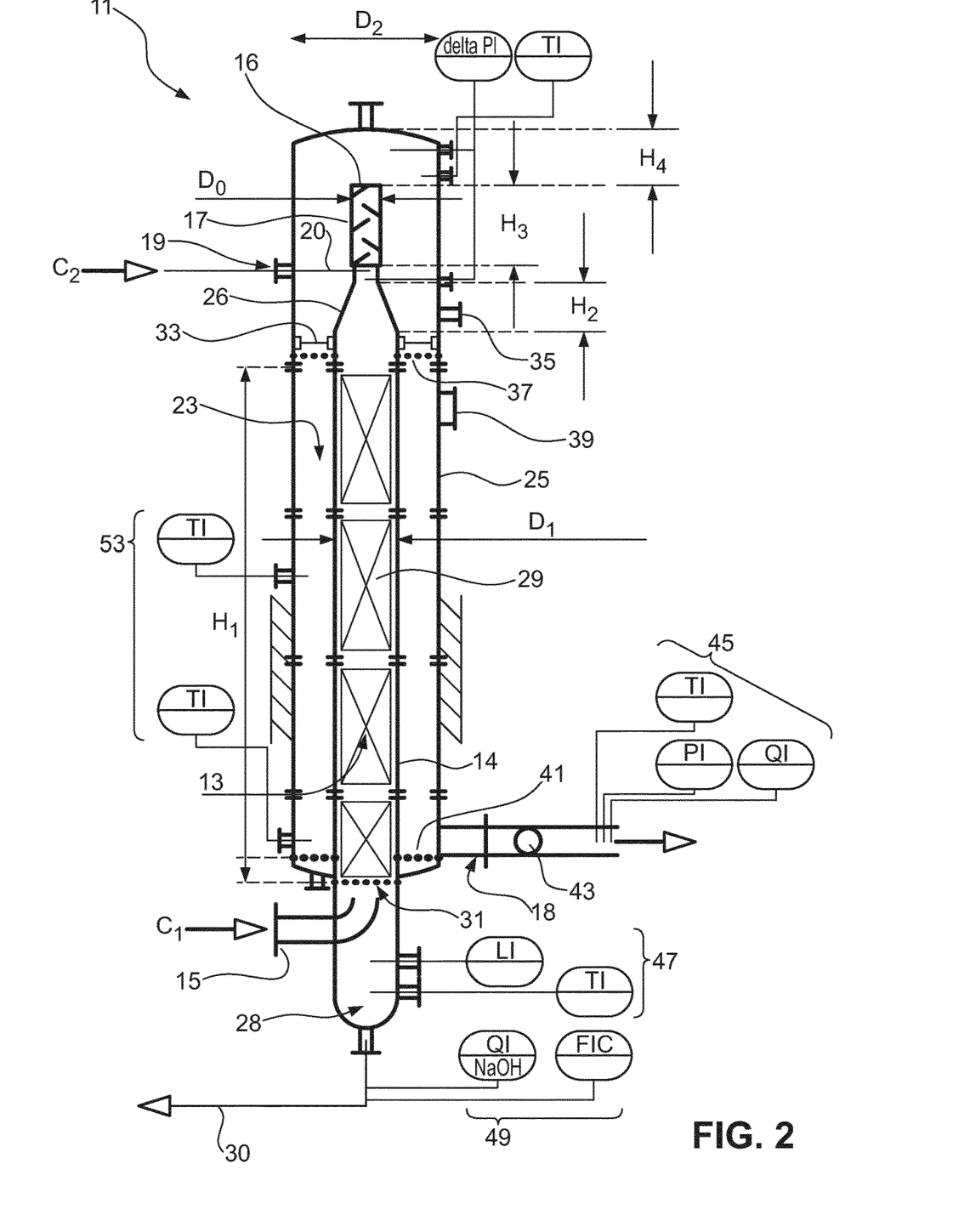
FIG. 2: is a schematic detail view of a reactor of the apparatus of FIG. 1.

In the embodiment shown in FIGS. 1 and 2, the first reactor chamber 13 is a vertical upward flow column, and the second reactor chamber 23 is a substantially annular vertical downward flow column. The flow velocity in the first reactor chamber 13 is significantly greater than the flow velocity in the second reactor chamber 23 due to the dimensioning of the reactor 11, as is seen in more detail in FIG. 2. Below the first inlet 15, the first reactor chamber 13 comprises a sump 28 for gathering liquid, and particularly water and/or hydroxide, and a drainage 30 for quickly removing material from the first reactor chamber 13 if need be.

FIG. 2 shows the reactor 11 of apparatus 1 in more detail. Inside the reactor 11, the first reactor chamber 13 is provided with a plurality of mixing elements 29, which preferably are stationary X-type mixing elements. The mixing elements 29 are distributed over a column height $H_1$. Downstream from the plurality of mixing elements 29, the first reactor chamber 31 is tapered along a length Hz. In between the section comprising the mixing elements 29 and the tapered section 26, the first reactor chamber 13 and its inner tube 14 are preferably fixed to the outer tube 25 with corresponding fixing means 33, for example a plurality of spokes.

The first reactor chamber 13 comprises a perforated cover sheet 31. The cover sheet 31 is configured to promote an even flow distribution across the chamber diameter, i. e. to promote breaking the directed flow ("jet") coming from the inlet tube by means of a pressure drop.

The first reactor chamber 13 has a diameter $D_1$ which is larger than a diameter $D_0$ of the mixing device 17, but smaller than a diameter $D_2$ of the outer tube 25 delimiting the second reactor chamber 23. Preferably, the diameter $D_2$ of the outer tube 25 is 1.5× to 3.0× the size of the diameter $D_1$ of the inner tube 14. The diameter $D_1$ of the inner tube 14 preferably is in the range of 3.0× to 5.0× the diameter $D_0$ of the mixing device.

The column height $H_1$ preferably is defined as a function of the diameter $D_1$ of the first reactor chamber. Preferably, the ratio $H_1/D_1$ is in a range of 15:1 or more, further preferred in a range of 25:1 or more.

The mixing device 17 has a length $H_3$ in the direction of flow. $H_3$ preferably is defined as a function of the diameter $D_0$ of the mixing device. Preferably, the ratio $H_3/D_0$ is in a range of 3:1 or more, further preferred in a range of 5:1 or more.

Above the outlet 16 of the mixing device 17, i.e. first reactor chamber 13, the second reactor chamber 23 preferably comprises a head room having a height $H_4$. $H_4$ preferably is defined as a function of the diameter $D_2$ of the outer tube 25. Preferably, the ratio $H_4/D_2$ is in a range of 3:2 or more, further preferred in a range of 5:2 or more.

The second reactor chamber 23 comprises at least one lateral port 35 for taking samples. Additionally, the second reactor chamber 23 preferably comprises a lateral opening 39 that can be reversibly opened and closed for inspection of the second reactor chamber 23, and/or for installing loose packing material into the annular portion of the second reactor chamber 23. The opening 39 may be a handhole or manhole.

The reactor 11 comprises a number of—i.e. one or a plurality of—perforated sheets, for example indicated by reference sign 41, in the annular section of the second reactor chamber 23 to delimit the volume in which packing material may be arranged. Further, reactor 11 comprises at least one cover sheet 37 configured to promote even flow distribution across the diameter of the annular portion.

In the outlet end of the second reactor chamber, downstream of the outlet 18, the apparatus 1 comprises an inspection glass 43 allowing for visual inspection of the material that is withdrawn from the reactor 11. Additionally, the reactor 11 may comprise a sensor assembly 45 for determining at least one of temperature, pressure and concentration of materials in the outlet feed.

Additionally, the reactor 11 may comprise a sensor assembly 47 arranged in the region of the sump 28 and configured to determine a liquid level and/or temperature and/or hydroxide concentration within the first reactor chamber in the region of the swamp 29. The drainage line 30 may further comprise a sensor assembly 49 configured to determine a hydroxide concentration and/or flow parameters.

Within the region potentially to be filled with packing material, the second reactor chamber 23 may also comprise a number of—i.e. one or a plurality of—temperature sensors 53.

In the following, preferred aspects A1 to A15 of the apparatus under the second perspective and of the process for making pseudoionone and hydroxy pseudoionone under the third perspective of the present invention are summarized:

Aspects:

A1. An apparatus (1) for producing pseudoionone and hydroxy pseudoionone, comprising
a first substantially vertically oriented reactor chamber (13) arranged such that components flow through the first reactor chamber in a first flow direction,
a second substantially vertically oriented reactor chamber (23) in fluid communication with the first reactor chamber (13), and the second reactor chamber (23) being oriented such that components flow through the second reactor chamber (23) in a second flow direction different from the first flow direction,
wherein
the first reactor chamber (13) is configured to receive a first component feed (C1) containing a first aqueous mixture through an inlet (15), and to produce a second aqueous mixture by allowing to react for a reaction time the components of the first aqueous mixture and wherein
the apparatus (1) comprises a mixing device (17) positioned downstream of the first component feed inlet (15) the first reactor chamber (13) and configured to add a second component feed (C2) to the first component feed (C1) when the second aqueous mixture has formed, and
the second reactor chamber (23) is configured to receive the first and second component feeds unified in the mixing device (17) from the first reactor chamber (13) and to produce a third aqueous mixture from the first and second aqueous mixtures.

A2. The apparatus (1) of aspect 1, wherein the first flow direction is oriented upwards, and the second flow direction is oriented downwards, or vice versa.

A3. The apparatus (1) of aspect 1 or 2, wherein the mixing device (17) is positioned on an outlet end of the first reactor chamber (13).

A4. The apparatus (1) of any one of aspects 1 to 3,
wherein the inlet (15) to the first reactor chamber (13) for receiving the first component feed (C1) is a first inlet, and the first reactor chamber (13) further comprises a second inlet (19) for receiving the second component feed (C2), wherein the second component feed (C2) is positioned upstream from the mixing device (17),
wherein preferably, the second inlet (19) is positioned immediately upstream of the mixing device (17), or at a predetermined distance upstream of the mixing device (17), wherein preferably, the distance is selected such that the entire second component feed (C2) is drawn into the mixing device (17) without prior backwards flow inside the first reactor chamber (13).

A5. The apparatus (1) of any one of the preceding aspects, wherein
the first reactor chamber (13) comprises a tapered section (26) upstream of and tapered towards the inlet of the mixing device (17), preferably immediately upstream of the second inlet, for accelerating the flow speed of the second aqueous mixture;
and/or
the first reactor chamber (13) comprises a number of further mixing elements (29) upstream of the mixing device (17), the mixing elements (29) configured to harmonize a residence time of the first component feed (01) between the inlet (16) to the first reactor and the mixing device (17);
and/or
the second reactor chamber (23) comprises an opening (39) that is configured to be reversibly opened and closed with a corresponding cover, the opening (39) being dimensioned for introducing a packing into the second reactor chamber (23), the packing preferably comprising or consisting of loose packing material.

A6. The apparatus (1) of any one of the preceding aspects, wherein the inlet for the first component feed (C1) is in fluid communication with a feed line (3), the feed line (3) being configured to generate the first component feed (C1) from a plurality of starter materials,
wherein preferably, the feed line (3) comprises a first mixer (5) and a second mixer (9), wherein the first mixer (5) is configured to combine a first starter material feed (S1) and a second starter material feed (S2), and the second mixer (9) is positioned downstream of the first mixer (5) and configured to combine the unified first and second starter feeds (S1+S2) coming from the first mixer (5) with a third starter material feed (S3) into the first component feed (C1).

A7. The apparatus (1) of aspect 6,
wherein the feed line (3) comprises at least one heating device (7), preferably at least one heat exchanger, configured to heat the first and second starter material feeds (S1, S2) to a predetermined temperature that is higher than a temperature of the third starter material feed (S3), wherein the at least one heating device preferably
is configured to heat the first and second starter materials as a function of the first, second and third starter material feed rates and the temperature of the third starter material feed such that the first component feed (C1) reaches a predetermined set point temperature prior to entering the first reactor chamber (13), and/or
is positioned in between the first and second mixers (5, 9).

A8. The apparatus (1) of any one of the preceding aspects, wherein at least one of the first and second reactor chambers (13, 23) is a reactor tube.

A9. The apparatus (1) of any one of the preceding aspects, wherein the second reactor chamber (23) is at least partially formed as a ring chamber.

A10. The apparatus (1) of aspects 8 and 9, wherein the first reactor chamber (13) and second reactor chamber (23) are part of one common reactor (11), said reactor (11) having an inner tube (14) and an outer tube (25), wherein the first reactor chamber (13) is delimited by a volume of the inner tube (14), and the second reactor chamber (23) is delimited by a volume of the outer tube (25) minus the volume of the inner tube (14).

A11. A process of making pseudoionone and hydroxy pseudoionone, preferably in an apparatus (1) of any one of the preceding aspects, comprising the steps of:
feeding a first component feed (C1) containing a first aqueous mixture into a first reactor chamber (13) through an inlet (15), the first aqueous mixture preferably comprising first concentrations of acetone, citral and hydroxide, preferably by combining first amounts of water, acetone, citral and hydroxide,
producing a second aqueous mixture by allowing to react for a reaction time the components of the first aqueous mixture, preferably so that pseudoionone, hydroxy pseudoionone and 4-hydroxy-4-methylpentan-2-one are formed, and acetone, citral, and hydroxide are consumed, the second aqueous mixture preferably comprising 4-hydroxy-4-methylpentan-2-one at a concentration which is higher than its concentration in the first aqueous mixture, acetone, citral and hydroxide at second concentrations which are lower than their first concentrations, and pseudoionone and hydroxy pseudoionone, and
adding a second component feed (C2) to the first component feed (C1), preferably a second amount of hydroxide, downstream of the first component feed inlet (15), in particular when the second aqueous mixture has formed,
supplying the first and second component feeds (C1+C2) to a second reactor chamber (23), and producing a third aqueous mixture by allowing the second aqueous mixture and the second component feed (C2) to react for a reaction time in the second reactor chamber (23), so that an additional amount of pseudoionone is formed in the third aqueous mixture in the second reactor chamber (23).

A12. The process of aspect 11, comprising one, several or all of the steps of:
accelerating the flow speed of the second aqueous mixture prior to adding the second component feed;
and/or
generating the first component feed (C1) by combining a first starter material feed (S1) and a second starter material feed (S2), and subsequently combining the unified first and second starter feeds with a third starter material feed (S3) into the first component feed (C1);
and/or
heating the first and second starter material feeds (S1, S2) to a predetermined temperature that is higher than a temperature of the third starter material feed (S3), preferably by heating the first and second starter materials as a function of the first, second and third starter material feed rates and the temperature of the third starter material feed such that the first component feed (C1) reaches a predetermined set point temperature prior to entering the first reactor chamber (13).

A13. The process of any one of aspects 11 or 12, further comprising one, more or all of the steps:
controlling a feed rate of the first component feed (C1) such that the first component feed (C1) has a predetermined residence time in the first reactor chamber (13) before reaching the second reactor chamber (23), preferably in the range of 3 minutes or more, further preferably 5 minutes or more;
and/or
harmonizing the residence time of the first component feed (C1) in the first reactor chamber (13) by providing a number of mixing elements (29);
and/or
providing a packing in the second reactor chamber (23);
and/or
determining a pressure difference between the first and second reactor chamber (23), preferably at a respective location upstream and downstream of the mixing device (17).

A14. The process of any one of aspects 11 to 13, further comprising the steps of:
b1) determining at least one of:
an amount of hydroxide unwantedly accumulating inside the first reactor chamber (13),
an amount of citral entering the first reactor chamber (13),
an amount of citral at the outlet or downstream of the first reactor chamber (13),
an amount of citral at the outlet or downstream of the second reactor chamber (23),
an amount of water at the outlet or downstream of the second reactor chamber (23),
an amount of at least one of pseudoionone or hydroxy pseudoionone at the outlet or downstream of the first reactor chamber (13),
an amount of at least one of pseudoionone or hydroxy pseudoionone at the outlet or downstream of the second reactor chamber (23);
the reactor feed temperature of at least one of the first or second component feeds,
the reactor residence time of at least one of the first or second component feeds; or
a feed rate of the first component feed (C1);
and
b2) if the amount or amounts determined in b1) fall outside of respective predetermined threshold ranges, increasing or decreasing at least one of:
the feed rate of the second component feed (C2) relative to the first component feed (C1), or
the feed rate of that starter material feed which comprises hydroxide, preferably the third starter material feed (S3), relative to the first component feed (C1) such that the amounts determined in b1) return to inside of the threshold range.

A15. A use of a system according to any one of aspects 1 to 10 for making pseudoionone and hydroxy pseudoionone.

The invention claimed is:
1. Process of making pseudoionone and hydroxy pseudoionone, comprising the following steps:
 (P1) preparing a first aqueous mixture comprising first concentrations of acetone, citral and hydroxide, by combining first amounts of water, acetone, citral and hydroxide,
 (P2) producing a second aqueous mixture by allowing to react for a reaction time the components of the first aqueous mixture so that
  pseudoionone, hydroxy pseudoionone and 4-hydroxy-4-methylpentan-2-one are formed, and
  acetone, citral and hydroxide are consumed,
  the second aqueous mixture comprising
  4-hydroxy-4-methylpentan-2-one at a concentration which is higher than its concentration in the first aqueous mixture,
  acetone, citral and hydroxide at second concentrations which are lower than their first concentrations, and
  pseudoionone and hydroxy pseudoionone,
 and
 (P3) producing a third aqueous mixture by adding to the second aqueous mixture a second amount of hydroxide so that an additional amount of pseudoionone is formed in the third aqueous mixture;
 wherein the second amount of hydroxide is added to the second aqueous mixture in step (P3) after 3 minutes or more of reaction time of the components of the first aqueous mixture in step (P2).
2. Process according to claim 1 wherein in step (P3):
 the second amount of hydroxide which is added to the second aqueous mixture is in the range of from 5 mass-% to 50 mass-%, of the first amount of hydroxide in the first aqueous mixture,
 and/or
 the concentration of dissolved hydroxide present in the third aqueous mixture is higher than the concentration of dissolved hydroxide present in the second aqueous mixture at the end of the reaction time.
3. Process according to claim 1 wherein the second amount of hydroxide is added to the second aqueous mixture in step (P3):
 when the molar concentration of 4-hydroxy-4-methylpentan-2-one in the second aqueous mixture has reached a value of 70 mmol/l or above;
 and/or
 before the concentration of 4-hydroxy-4-methylpentan-2-one in the second aqueous mixture has reached a maximum or when the concentration of 4-hydroxy-4-methylpentan-2-one in the second aqueous mixture has reached a maximum;
 and/or
 when the concentration of 4-hydroxy-4-methylpentan-2-one in the second aqueous mixture has a value of ≥80% of its maximum value;
 and/or
 3 minutes or more after the first aqueous mixture has been prepared;
 and/or
 when the molar ratio of 4-hydroxy-4-methylpentan-2-one:acetone in the second aqueous mixture has reached a value in the range of from 1:45 to 1:8.

4. Process according to claim 1, wherein the first aqueous mixture and/or the second aqueous mixture and/or the third aqueous mixture are mixed or agitated mechanically.
5. Process according to claim 1 wherein
 at least a part of the process is conducted continuously;
 and/or
 the second amount of hydroxide is added to the second aqueous mixture continuously.
6. Process according to claim 1, wherein at least a part of the process is conducted in batch-mode or semi-batch mode.
7. Process according to claim 1, wherein the second amount of hydroxide is added to the second aqueous mixture in one single portion or in several individual portions.
8. Process according to claim 1, wherein the total amount of pseudoionone formed in a sequence of steps (P2) and (P3) in a reaction time t [(P2)+(P3)] is higher than the total amount of pseudoionone formed in an isolated step (P2) in an equal reaction time t [(P2)+(P3)].
9. Process according to claim 1, wherein the total process time is in the range of from ≥9 to ≤30 minutes.
10. Process according to claim 1, wherein
 the first concentration of the hydroxide in the first aqueous mixture is in the range of from 0.0015 to 0.02 mass-%, relative to the total mass of water and acetone present in the first aqueous mixture;
 and/or
 the molar ratio of the first amount of hydroxide present in the first aqueous mixture relative to the first amount of citral present in the first aqueous mixture is in the range of from 1.0 to 30.0 mmole/mole;
 and/or
 the molar ratio of the total amount of acetone present in the first aqueous mixture relative to the total amount of citral present in the first aqueous mixture is in the range of from 24.0:1 to 65.5:1.
11. Process according to claim 1, wherein the first amount of hydroxide which is used to prepare the first aqueous mixture and/or the second amount of hydroxide which is added to the second aqueous mixture is provided by one or more metal hydroxides.
12. Process according to claim 1, wherein the first aqueous mixture and/or the second aqueous mixture and/or the third aqueous mixture form liquid phases below their boiling points.
13. Process according to claim 1, wherein the reaction conditions, are selected or adjusted so that the first aqueous mixture forms a single liquid phase and/or the second aqueous mixture forms a single liquid phase and/or the third aqueous mixture forms a single liquid phase.
14. Process according to claim 1, wherein the total amount of hydroxide present in the third aqueous mixture is dissolved in the liquid phase.
15. Process according to claim 1, wherein the first aqueous mixture comprises water in a concentration in the range of from 3 to 9 mass-%, relative to the total mass of water and acetone present in the first aqueous mixture.
16. Process according to claim 1, wherein the first amount of hydroxide which is used to prepare the first aqueous mixture and/or the second amount of hydroxide which is added to the second aqueous mixture is provided by one or more metal hydroxides,
 wherein
  the one or more metal hydroxides are selected from the group consisting of:
   LiOH, NaOH and KOH; and
   $Mg(OH)_2$, $Ca(OH)_2$, $Sr(OH)_2$ and $Ba(OH)_2$;
  and/or the one or more metal hydroxides comprise one or more metal hydroxides dissolved in a liquid phase,
wherein the aqueous solution has a concentration of hydroxide ions in the range of from 0.3 to 1.5 mass-%, relative to the total mass of water and metal hydroxides present in the aqueous solution.

17. Process according to claim 1, wherein the first aqueous mixture and/or the second aqueous mixture and/or the third aqueous mixture form liquid phases below their boiling points and wherein
- the reaction temperature in the first aqueous mixture and/or in the second aqueous mixture and/or in the third aqueous mixture is in the range of from 60 to 110° C.;

and/or
- the entire process is conducted at a pressure in the range of from 150 to 1000 kPa;

and/or
the entire process is conducted under adiabatic conditions.

18. Process according to claim 1,
wherein
- the first concentration of the hydroxide in the first aqueous mixture is in the range of from 0.0015 to 0.0140 mass-%, relative to the total mass of water and acetone present in the first aqueous mixture;

and/or
- the molar ratio of the first amount of hydroxide present in the first aqueous mixture relative to the first amount of citral present in the first aqueous mixture is in the range of from 2.0 to 20.0 mmole/mole;

and/or
- the molar ratio of the total amount of acetone present in the first aqueous mixture relative to the total amount of citral present in the first aqueous mixture is in the range of from 31.5:1 to 65.5:1.

19. Process according to claim 1 wherein the second amount of hydroxide is added to the second aqueous mixture in step (P3):

when the molar concentration of 4-hydroxy-4-methylpentan-2-one in the second aqueous mixture has reached a value of 70 mmol/l or above;

and/or
before the concentration of 4-hydroxy-4-methylpentan-2-one in the second aqueous mixture has reached a maximum or when the concentration of 4-hydroxy-4-methylpentan-2-one in the second aqueous mixture has reached a maximum;

and/or
when the concentration of 4-hydroxy-4-methylpentan-2-one in the second aqueous mixture has a value of ≥85% of its maximum value;

and/or
5 minutes or more, after the first aqueous mixture has been prepared, and less than 25 minutes after the first aqueous mixture has been prepared;

and/or
after 5 minutes or more, of reaction time of the components of the first aqueous mixture in step (P2),
and after less than 25 minutes, of reaction time of the components of the first aqueous mixture in step (P2);

and/or
when the molar ratio of 4-hydroxy-4-methylpentan-2-one:acetone in the second aqueous mixture has reached a value in the range of from 1:45 to 1:8.

20. Process according to claim 1
wherein in step (P3):
- the second amount of hydroxide which is added to the second aqueous mixture is in the range of from 10 mass-% to 40 mass-%, of the first amount of hydroxide in the first aqueous mixture, and/or
the concentration of dissolved hydroxide present in the third aqueous mixture is higher than the concentration of dissolved hydroxide present in the second aqueous mixture at the end of the reaction time.

* * * * *